United States Patent
Sugahara et al.

(10) Patent No.: US 6,303,631 B1
(45) Date of Patent: Oct. 16, 2001

(54) WATER-SOLUBLE EYE DROP

(75) Inventors: Yuji Sugahara; Kazuya Sakata, both of Itano-gun; Masaaki Odomi, Tokushima, all of (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/582,030

(22) PCT Filed: Dec. 16, 1998

(86) PCT No.: PCT/JP98/05699

§ 371 Date: Jan. 21, 2000

§ 102(e) Date: Jan. 21, 2000

(87) PCT Pub. No.: WO99/32087

PCT Pub. Date: Apr. 1, 1999

(30) Foreign Application Priority Data

Dec. 22, 1997 (JP) .................................................... 9-353039
Oct. 20, 1998 (JP) .................................................. 10-298550

(51) Int. Cl.⁷ .................................................... A61K 31/47
(52) U.S. Cl. ........................ 514/312; 514/772.3; 514/912
(58) Field of Search .................................... 514/312, 912, 514/772.3

(56) References Cited

U.S. PATENT DOCUMENTS

| 4,309,432 | 1/1982 | Tanaka et al. . |
| 5,461,081 | 10/1995 | Ali et al. ............................ 514/772.3 |

FOREIGN PATENT DOCUMENTS

| 2 007 091 | 5/1979 | (GB) . |
| WO 94/04134 | 3/1994 | (WO) . |
| WO 95/26712 | 10/1995 | (WO) . |

OTHER PUBLICATIONS

F. Thermes et al., "Bioadhesion: The Effect of Polyacrylic Acid on the Ocular Bioavailability of Timolol", International Journal of Pharmaceutics, vol. 81, No. 1, pp. 59–65, (1992).

*Primary Examiner*—Zohreh Fay
(74) *Attorney, Agent, or Firm*—Finnegan, Henderson, Farabow, Garrett & Dunner L.L.P.

(57) ABSTRACT

A water-soluble eye drop comprising (a) at least one selected from carteolol and an acid addition salt thereof, (b) at least one acrylic polymer selected from a straight-chain type polyacrylic acid and a pharmaceutically acceptable water-soluble salt thereof, and (c) at least one selected from a water-soluble alkali metal salt and a water-soluble amine. The water soluble eye drop has a remarkably long duration time of drug efficacy, and is superior in intraocular pressure inhibition action and is effective for treatment of glaucoma.

13 Claims, No Drawings

WATER-SOLUBLE EYE DROP

TECHNICAL FIELD

The present invention relates to a water-soluble eye drop. More particularly, it relates to a water-soluble eye drop which has a remarkably long duration time of drug efficacy, and which is superior in an intraocular pressure inhibition action and is effective for treatment of glaucoma.

BACKGROUND ART

It has been well known that a carbostyryl derivative represented by the formula (1):

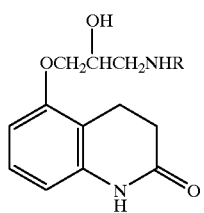

(1)

wherein R represents a tert-butyl group, or an acid addition salt thereof is a compound which is effective as a remedy for glaucoma (U.S. Pat. No. 4,309,432). The compound represented by the above formula (1) is referred to as carteolol.

On the other hand, an eye drop or an ophthalmic ointment is often used as the eye drop.

In case of the eye drop, since a base is usually purified water, it is difficult to adhere the eye drop onto the cornea in the case of dropping it in the eyes. Furthermore, it is impossible to avoid that the eye drop is diluted with lacrimal fluid and falls from the eyes. Accordingly, it was difficult for a conventional eye drop to sufficiently retain a drug in the eye drop in the eyes.

Furthermore, the ophthalmic ointment is prepared by adding liquid paraffin, purified lanolin or the like to petrolatum as a base. Such an ophthalmic ointment is liable to be discharged from the eyes by means of lacrimal fluid because of its poor hydrophilicity. Therefore, there is such a drawback that the opthalimic ointment is not sufficiently adhered onto the cornea and ophthalmic mucosa and, as a result, the amount of the drug in the ophthalmic ointment, which arrives the affected part and is absorbed, is small. The ophthalmic ointment also has a drawback that an unpleasant feel arises in the eyes after applying it because of oiliness of an oily base.

To solve the above drawbacks of the conventional eye drop and ophthalmic ointment, British Patent No. 2,007,091 corresponding to Japanese Patent Laid-Open Publication No. 67021/1979 suggests a gelled eye drop. The gelled eye drop described in said publication is an eye drop prepared by mixing an aqueous crosslinked type polyacrylic acid solution with a water-soluble basic substance and a drug for eye drop, which has the pH of 5 to 8 and the viscosity of 1,000 to 100,000 centipoise at 20° C.

However, such a gelled eye drop is insufficient in duration time of drug efficacy, and is inferior in intraocular pressure inhibition action. Furthermore, the gelled eye drop is also insufficient in ease of handling and affinity to the eyes (feeling in the case of dropping it in the eyes). Accordingly, it is difficult to use such a gelled eye drop as an eye drop which is particularly effective for treatment of glaucoma requiring the control of the intraocular pressure.

SUMMARY OF THE INVENTION

To develop a water-soluble eye drop having no drawbacks described above, the present inventors have intensively studied. As a result, they have found that a water-soluble eye drop comprising the following component (a), component (b) and component (c) can be used as a desired water-soluble eye drop having no drawbacks described above.

That is, the present invention relates to a water-soluble eye drop comprising (a) at least one selected from carteolol and an acid addition salt thereof, (b) at least one acrylic polymer selected from a straight-chain type polyacrylic acid and a pharmaceutically acceptable water-soluble salt thereof, and (c) at least one selected from a water-soluble alkali metal salt and a water-soluble amine.

Although a base is purified water, the eye drop of the present invention is easily applied onto the cornea in the case of dropping it in the eyes and is not likely to fall from the eyes even if the eye drop is diluted with lacrimal fluid. Accordingly, according to the eye drop of the present invention, a drug component in the eye drop in the eye drop can be retained sufficiently in the eyes.

The water-soluble eye drop of the present invention has a remarkably long duration time of drug efficacy, and is superior in intraocular pressure inhibition action. Accordingly, the water-soluble eye drop of the present invention is an eye drop which is particularly effective for treatment of glaucoma requiring the control of the intraocular pressure.

Furthermore, the water-soluble eye drop of the present invention is satisfactory in ease of handling and affinity to the eyes (feeling in the case of dropping it in the eyes).

DETAILED DESCRIPTION OF THE INVENTION

The water-soluble eye drop of the present invention includes embodiments described hereinafter.

1) A water-soluble eye drop comprising (a) at least one selected from carteolol and an acid addition salt thereof, (b) at least one acrylic polymer selected from a straight-chain type polyacrylic acid and a pharmaceutically acceptable water-soluble salt thereof, and (c) at least one selected from a water-soluble alkali metal salt and a water-soluble amine.

2) The water-soluble eye drop according to the above item 1), wherein the component (a) and the component (b) are contained in the amount of about 0.1 to 5% by weight and the amount of about 0.3 to 10% by weight, respectively, and the concentration of the component (c) is from-about 10 to 140 mmol.

3) The water-soluble eye drop according to the above item 2), wherein the pH of the water-soluble eye drop is from about 4 to 10 and the viscosity at 25° C. of the water-soluble eye drop is from about 5 to 100 centipoise and, furthermore, the viscosity-average molecular weight of the acrylic polymer of the component (b) is from about 100,000 to 3,000,000.

4) The water-soluble eye drop according to the above item 3), wherein the pH of the water-soluble eye drop is from about 5 to 9 and the viscosity at 25° C. of the water-soluble eye drop is from about 10 to 70 centipoise and, furthermore, the viscosity-average molecular weight of the acrylic polymer of the component (b) is from about 2,000,000 to 3,000,000.

5) The water-soluble eye drop according to the above item 2), wherein the component (a) and the component (b) are contained in the amount of about 0.5 to 3% by weight and the amount of about 0.3 to 0.5% by weight, respectively, and the concentration of the component (c) is from about 30 to 120 mmol.

6) The water-soluble eye drop according to the above item 5), wherein the pH of the water-soluble eye drop is from about 4 to 10 and the viscosity at 25° C. of the water-soluble eye drop is from about 5 to 100 centipoise and, furthermore, the viscosity-average molecular weight of the acrylic polymer of the component (b) is from about 100,000 to 3,000,000.

7) The water-soluble eye drop according to the above item 5), wherein the pH of the water-soluble eye drop is from about 5 to 9 and the viscosity at 25° C. of the water-soluble eye drop is from about 10 to 70 centipoise and, furthermore, the viscosity-average molecular weight of the acrylic polymer of the component (b) is from about 2,000,000 to 3,000,000 and sodium chloride as the component (c) is contained in the amount of about 0.05 to 0.8% by weight.

8) The water-soluble eye drop according to the above item 1), wherein the pH of the water-soluble eye drop is from about 4 to 10 and the viscosity at 25° C. of the water-soluble eye drop is from about 5 to 100 centipoise and, furthermore, the viscosity-average molecular weight of the acrylic polymer of the component (b) is from about 100,000 to 3,000,000.

9) The water-soluble eye drop according to the above item 8), wherein the. pH of the water-soluble eye drop is from about 5 to 9 and the viscosity at 25° C. of the water-soluble eye drop is from about 10 to 70 centipoise and, furthermore, the viscosity-average molecular weight of the acrylic polymer of the component (b) is from about 2,000,000 to 3,000,000.

10) The water-soluble eye drop according to the above item 1), wherein the component (a) is carteolol hydrochloride.

11) The water-soluble eye drop according to the above item 1), wherein the component (b) is sodium polyacrylate.

12) The water-soluble eye drop according to the above item 1), wherein the component (c) is a water-soluble alkali metal salt.

13) The water-soluble eye drop according to the above item 12), wherein the water-soluble alkali metal salt is sodium chloride or potassium chloride.

BEST MODE FOR CARRYING OUT THE INVENTION

The component (a) to be mixed with the water-soluble eye drop of the present invention is at least one selected from carteolol and an acid addition salt thereof.

The chemical name of carteolol is 5-(2-hydroxy-3-tert-butylamino)propoxy-3,4-dihydrocarbostyryl.

The acid addition salt of carteolol includes pharmaceutically acceptable acid addition salts, for example, salts of hydrochloric acid, sulfuric acid, nitric acid, hydrobromic acid, oxalic acid, maleic acid, fumaric acid, citric acid and tartaric acid.

In the present invention, 5-(2-hydroxy-3-tert-butylamino)propoxy-3,4-dihydrocarbostyryl hydrochloride (carteolol hydrochloride) is particularly preferred as the component (a).

The component (b) to be mixed with the water-soluble eye drop of the present invention is at least one acrylic polymer selected from a straight-chain type polyacrylic acid and a pharmaceutically acceptable water-soluble salt thereof.

In the present invention, the straight-chain type polyacrylic acid has a repeating unit shown below.

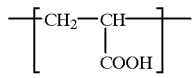

The pharmaceutically acceptable water-soluble salt of the straight-chain type polyacrylic acid is prepared by neutralizing a carboxyl group of the above repeating unit with basic substances, for example, alkali metal hydroxides such as sodium hydroxide, potassium hydroxide and the like. The neutralization degree may be any of complete neutralization and partial neutralization, but complete neutralization is preferred.

The pharmaceutically acceptable water-soluble salt of the straight-chain type polyacrylic acid is preferably sodium polyacrylate.

The molecular weight of the acrylic polymer as the component (b) is not specifically limited, but the viscosity-average molecular weight is usually from about 100,000 to 3,000,000, and preferably from about 2,000,000 to 3,000,000.

Specific examples of the straight-chain type polyacrylic acid include Aqualic HL-521, AS-52, AS-58 and HL-580 manufactured by Nippon Shokubai Co., Ltd.; Jurimer AC-10SHP and AC-10LHP manufactured by Nihon Junyaku Co., Ltd.; and A-10H and A-10HL manufactured by TOAGOSEI CO., LTD. Specific examples of the sodium salt of the straight-chain type polyacrylic acid include Aqualic DL-522, IH-K, IH-L and FH-K manufactured by Nippon Shokubai Co., Ltd.; Aronbis S, SS, GL, M and MS manufactured by Nihon Junyaku Co., Ltd.; A-7100, A-7100G (F), A-20L, A-20LH, A-20P (H), A-20P, A-20PG, A-20P (3) and A-20PX manufactured by TOAGOSEI CO., LTD.; and sodium polyacrylate manufactured by Wako Pure Chemical Industries, Ltd. During the long-term storage of the water-soluble eye drop, white turbidity is caused, sometimes, by the kind of additives to be added in the industrial production process of the acrylic polymer and residue thereof. Therefore, it is particularly preferred to use an acrylic polymer which does not cause white turbidity.

The component (b) is preferably a straight-chain type sodium polyacrylate which does not cause white turbidity of the water-soluble eye drop during the long-term storage, particularly straight-chain type sodium polyacrylate which does not use an additive causing white turbidity in the production process, and more specifically Aqualic FH-K manufactured by Nippon Shokubai Co., Ltd.

The component (c) to be mixed with the water-soluble eye drop of the present invention is at least one selected from a water-soluble alkali metal salt and a water-soluble amine. The water-soluble alkali metal salt includes, for example, chloride of alkali metal, carbonate of alkali metal and alkali metal salt of organic acid. Specific examples of the chloride of the alkali metal include sodium chloride, potassium chloride and the like. Specific examples of the carbonate of the alkali metal include sodium carbonate, potassium carbonate and the like. Specific examples of the alkali metal salt of the organic acid include sodium acetate, potassium acetate, sodium citrate, potassium citrate and the like.

The water-soluble amine includes, for example, monoalkylamine, dialkylamine, trialkylamine, monoalkanolamine, dialkanolamine, trialkanolamine and trimethylolaminomethane. Specific examples of the monoalkylamine include methylamine, ethylamine, propylamine and the like. Specific examples of the dialkylamine include dimethylamine, diethylamine, dipropylamine and the like. Specific examples of the trialkylamine include trimethylamine, triethylamine, tripropylamine and the like. Specific examples of the monoalkanolamine include methanolamine, ethanolamine, propanolamine and the like. Specific examples of the dialkanolamine include dimethanolamine, diethanolamine, dipropanolamine, dibutanolamine and the like. Specific examples of the trialkanolamine include trimethanolamine, triethanolamine, tripropanolamine, tributanolamine and the like.

Among the water-soluble alkali metal salts and water-soluble amines, the water-soluble alkali metal salt is preferred and the chloride of the alkali metal, such as sodium chloride and potassium chloride is particularly preferred.

In the case of the water-soluble eye drop of the present invention, the viscosity at 25° C. is usually from about 5 to 100 centipoise, and preferably from about 10 to 70 centipoise. In the present invention, the viscosity of the water-soluble eye drop was measured by using a rotational viscometer RE-110SL (manufactured by Toki Sangyo Co., Ltd.). When the viscosity of the eye drop becomes too large, it becomes difficult to exert the effect as one of the features of the present invention, such as ease of handling and affinity to the eyes (feeling in the case of dropping it in the eyes). To the contrary, when the viscosity of the eye drop becomes too small, the duration time of drug efficacy is liable to be reduced.

The amount of the component (a) to be mixed with the water-soluble eye drop of the present invention is usually from about 0.1 to 5% by weight, and preferably from about 0.5 to 3% by weight.

The amount of the component (b) to be mixed with the water-soluble eye drop of the present invention is usually from about 0.3 to 10% by weight, and preferably from about 0.3 to 0.5% by weight. The amount of the component (b) varies depending on the viscosity-average molecular weight of the acrylic polymer to be used, but it is preferably mixed so that the viscosity at 25° C. of the resulting water-soluble eye drop is within a range from 5 to 100 centipoise as mentioned above.

The component (c) is mixed with the water-soluble eye drop of the present invention so that the concentration in the eye drop is usually within a range from about 10 to 140 mmol, and preferably from about 30 to 120 mmol. The component (c) is used to enhance the solubility of the component (b) in water, but it also serves as an isotonicity. In the present invention, the component (c) is preferably used in the amount enough to make the eye drop isotonic when the component (c) is combined with the component (a). Such an amount varies depending on the kind of the component (c) and can not be decided completely. For example, in the case of sodium chloride, the amount is usually from about 0.05 to 0.8% by weight, and preferably from about 0.2 to 0.54% by weight. When the other isotonicity such as D-mannitol is further mixed, together with the component (c), the amount of the component (c) can also be reduced according to the amount of the isotonicity.

The eye drop of the present invention is produced, for example, by mixing a predetermined amount of the above components (a) to (c) with sterile distilled water as a base and subjecting the solution to a sterilization treatment.

It is possible to further mix isotonicities, buffering agents, pH adjustors, solubilizers, stabilizers, antioxidants and antiseptics with the eye drop of the present invention.

The isotonicity includes, for example, a conventionally known one such as D-mannitol, glucose and glycerin.

The buffering agent includes, for example, a conventionally known one such as sodium dihydrogen phosphate, sodium hydrogen phosphate, potassium dihydrogen phosphate, potassium hydrogen phosphate, boric acid, sodium borate, citric acid, tartaric acid and sodium tartrate.

The pH adjustor includes, for example, a conventionally known one such as acid (e.g. hydrochloric acid, acetic acid, etc.) and base (e.g. sodium hydroxide, potassium hydroxide, etc.).

The solubilizer includes, for example, a conventionally known one such as polyoxyethylene glycol ethers (e.g. sodium carboxymethylcelullose, polyoxyethylene lauryl ether, polyoxyethylene oleyl ether, etc.), polyethylene glycol higher fatty acid esters (e.g. polyethylene glycol monolaurate, polyethylene glycol monooleate, etc.) and polyoxyethylene fatty acid esters (e.g. polyoxyethylene sorbitan monolaurate, polyoxyethylene sorbitan monooleate, etc.).

The stabilizer includes, for example, a conventionally known one such as hydroxypropylmethylcellulose, polyvinyl alcohol, carboxymethylcellulose, hydroxyethylcellulose, glycerin and EDTA.

The antioxidant includes, for example, sodium bisulfite, sodium thiosulfate and ascorbic acid.

The antiseptic includes, for example, a conventionally known one such as chlorobutanol, benzalkonium chloride, cetylpyridinium chloride, thimerosal, phenethyl alcohol, methyl paraben and propyl paraben.

The pH of the water-soluble eye drop of the present invention is usually from about 4 to 10, and preferably from about 5 to 9. When the pH exceeds 10, there is a fear that the component (a) is deposited in the eye drop of the present invention. On the other hand, when the pH is smaller than 4, there is a fear that the component (b) is deposited in the eye drop of the present invention.

It is preferred that the water-soluble eye drop of the present invention and lacrimal fluid are isotonic. The water-soluble alkali metal salt as the component (c) of the present invention serves as an isotonicity, and various isotonicities described above may be further mixed. It is particularly preferred that the pH of the water-soluble eye drop of the present invention is adjusted within a range from about 5.5 to 8.5, and preferably from about 6.5 to 7.5.

The water-soluble eye drop of the present invention is used in the same manner as that in the case of a conventionally known eye drop. For example, the water-soluble eye drop is preferably dropped in the eyes from a suitable eye drop container, or sprayed the eyes using a spraying device.

EXAMPLES

The following Examples further illustrate the present invention in more detail. In the following Examples, percentages are by weight unless otherwise stated.

Preparation Example 1

| | |
|---|---|
| Carteolol hydrochloride | 2% |
| Sodium polyacrylate | 0.4% |
| Sodium chloride | 0.2% |

-continued

| | |
|---|---|
| D-mannitol | 2% |
| Sterile distilled water | 95.4% |
| Total | 100% |

A 0.8% sodium polyacrylate solution was previously prepared by adding 0.8 g of a straight-chain type sodium polyacrylate [trade name: Aronbis MS manufactured by Nihon Junyaku Co., Ltd., viscosity-average molecular weight: 2,000,000 to 3,000,000] to 99.2 g of an aqueous sodium chloride solution, which is obtained by dissolving 0.4 g of sodium chloride in 98.8 g of sterile distilled water, and dissolving the straight-chain type sodium polyacrylate using a stirrer.

Two (2) g of D-mannitol was added to 40 g of an aqueous solution of carteolol hydrochloride prepared in the concentration of 5% and dissolved using a stirrer and, after confirming that D-mannitol was sufficiently dissolved, 50 g of the 0.8% sodium polyacrylate solution prepared previously and 8 g of sterile distilled water were added. They were dissolved by sufficiently stirring to obtain a water-soluble eye drop (preparation No. 1) of the present invention.

The pH of the resulting water-soluble eye drop was 8.0 and the viscosity at 25° C. was 20 centipoise.

The pH was measured by using a pH meter (HORIBA, pH meter M-8AD). The viscosity was measured at 25° C. by pouring 1–1.2 ml of the above water-soluble eye drop into a sample cup, using a rotational viscometer RE-110SL (manufactured by Toki Sangyo Co., Ltd.).

Comparative Preparation Examples

Various eye drops (preparation Nos. 2 to 11) were produced by mixing carteolol hydrochloride, water-soluble polymer compounds shown in Table 1 below, sodium chloride and other additives (isotonicity, buffering agent and pH adjustor) in a predetermined amount in accordance with the above Preparation Example. In Table 1, percentages are by weight based on the preparation, and "mM" means a millimolar concentration of sodium chloride based on the preparation.

The measurement results of the pH and viscosity at 25° C. of these eye drops are shown in Table 1.

TABLE 1

| Preparation No. | Carteolol hydrochloride | Water-soluble polymer compound | Sodium chloride | Others (isotonicity, buffering agent, pH adjustor) | pH | Viscosity (cps) |
|---|---|---|---|---|---|---|
| 1 | 2% | Sodium polyacrylate 0.4% | 0.2% (34.2 mM) | D-mannitol 2% | 8.0 | 20 |
| 2 | 2% | No addition of polymer (control) | 0.54% (92.4 mM) | 5 mM-phosphate buffer solution 5 mM | 6.7 | 1 |
| 3 | 2% | Sodium polyacrylate 0.9% | — | D-mannitol 2.5% | 8.3 | 14 |
| 4 | 2% | Sodium polyacrylate 0.9% | — | D-mannitol 2.5% Hydrochloric acid (q.s.) | 6.7 | 12 |
| 5 | 2% | Sodium dextran sulfate 5% | — | D-mannitol 2% | 6.7 | 24 |
| 6 | 2% | Sodium polystyrene sulfonate 5% | — | D-mannitol 2% | 7.0 | 43 |
| 7 | 2% | Potassium polyvinyl sulfate 5% | — | D-mannitol 1.9% | 6.7 | 20 |
| 8 | 2% | Sodium chondroitin sulfate 5% | — | D-mannitol 1.2% | 5.8 | 33 |
| 9 | 2% | Sodium hyaluronate 0.2% | — | D-mannitol 3.1% | 5.9 | 23 |
| 10 | 2% | Sodium hyaluronate 0.3% | — | D-mannitol 3.1% | 5.9 | 27 |
| 11 | 2% | Carboxyvinyl polymer (cross-linked type) 1.25% | 0.52% (90 mM) | Sodium hydroxide (q.s.) | 5.0 | 113 |

The water-soluble polymer compounds listed in Table 1 are as follows.

Sodium polyacrylate mixed with the preparations No. 3 and No. 4: trade name "Sodium Polyacrylate" manufactured by Wako Pure Chemical Industries, Ltd., viscosity-average molecular weight: about 250,000 to about 750,000.

Sodium dextran sulfate mixed with the preparation No. 5: trade name "DS-500" manufactured by Meito Sangyo Co., Ltd., viscosity-average molecular weight: about 500,000.

Sodium polystyrene sulfonate mixed with the preparation No. 6: trade name "PS-100" manufactured by TOSOH CORPORATION, viscosity-average molecular weight: about 1,100, 000.

Potassium polyvinyl sulfate mixed with the preparation No.7: trade name "Potassium Polyvinyl Sulfate" manufactured by Wako Pure Chemical Industries, Ltd., viscosity-average molecular weight: about 240,000.

Sodium chondroitin sulfate mixed with the preparation No. 8: trade name "Sodium Chondroitin Sulfate for "SEIKAGAKU" for injection"manufactured by SEIKAGAKU CORPORATION, viscosity-average molecular weight: about 40,000.

Sodium hyaluronate mixed with the preparation No. 9: trade name "Hyaluronic Acid HA-QSS" manufactured by Kewpie Co., Ltd., viscosity-average molecular weight: about 2,800,000.

Sodium hyaluronate mixed with the preparation No. 10: trade name "Hyaluronic Acid HA-Q" manufactured by Kewpie Co., Ltd., viscosity-average molecular weight: about 1,150,000.

Carboxyvinyl polymer mixed with the preparation No. 11: trade name "Noveon AA1" manufactured by BF Goodrich Co.

Preparation Example 2

According to the same manner as that described in Preparation Example 1 except for using sodium polyacrylate [trade name: Aqualic FH-K manufactured by Nippon Shokubai Co., Ltd., viscosity-average molecular weight: 2,000,000 to 3,000,000] as the straight-chain type sodium polyacrylate, a water-soluble eye drop (preparation No. 12) of the present invention was obtained.

The pH of the resulting water-soluble eye drop was 8.0 and the viscosity at 25° C. was 20 centipoise.

Experiment Example 1

Using various eye drops (preparations No.1 to No. 11) obtained above, the concentration (ng/ml) of the drug (carteolol hydrochloride) in the aqueous humor of house rabbit was determined in accordance with the following method.

That is, a white rabbit was fixed to a fixing device, and various eye drops (50 µl each) were dropped in both eyes. Four and eight hours after dropping in the eyes, the white rabbit was slaughtered by injecting barbital. The eye ball surface was washed with an isotonic sodium chloride solution and the aqueous humor was extracted, and then the concentration of the drug (ng/ml) in the aqueous humor was measured by reversed phase HPLC. The concentration of the drug in the aqueous humor of the house rabbit after 4 hour and 8 hours have passed since the eye drop was dropped in the eyes are shown in Table 2.

TABLE 2

| Preparation No. | Concentration of drug in aqueous humor after dropping eye drop in the eyes (ng/ml) | |
|---|---|---|
| | After 4 hours | After 8 hours |
| 1 | 2078 | 1127 |
| 2 | 361 | 52 |
| 3 | 1415 | 405 |
| 4 | 1298 | 177 |
| 5 | 596 | — |
| 6 | 333 | — |
| 7 | 514 | — |
| 8 | 688 | — |
| 9 | 672 | — |
| 10 | 699 | — |

The followings are apparent from Table 2.

In the case of a control (preparation No. 2) wherein the water-soluble polymer compound is not mixed, the concentration of the drug in the aqueous humor after 4 hours have passed since the eye drop was dropped in the eyes is 361 ng/ml, whereas, in the case of the eye drop (preparation No. 1) of the present invention, the concentration of the drug in the aqueous humor after 4 hours have passed since the eye drop was dropped in the eyes is 2078 ng/ml, that is, the concentration increased by about six times. On the other hand, in the case of the eye drops (preparations No. 3 to No. 10) of the Comparative Examples, the concentration of the drug in the aqueous humor after 4 hours have passed since the eye drop was dropped in the eyes increased by about 1–4 times compared with the control.

After 8 hours have passed since the eye drop was dropped in the eyes, the drug concentration was very high in the case of using the eye drop (preparation No. 1) of the present invention, and was superior in duration of drug efficacy.

The data in the case of using the preparation No. 11 is not shown in Table 2, but it was confirmed that the preparation No. 11 is inferior in duration of drug efficacy.

Preparation Example 3

The water-soluble alkali metal or water-soluble amine shown in Table 3 below was added to carteolol hydrochloride and sodium polyacrylate [trade name: Aronbis MS manufactured by Nihon Junyaku Co., Ltd., viscosity-average molecular weight: 2,000,000 to 3,000,000], followed by mixing in a rotator for about 12 hours. Thereafter, clarity and color of the solution were visually confirmed. Carteolol hydrochloride and sodium polyacrylate were used in such an amount that the concentration of carteolol hydrochloride and that of sodium polyacrylate in the eye drop are 2% and 0.5%, respectively. The water-soluble alkali metal salt or water-soluble amine was used in such an amount that the resulting eye drop is nearly isotonic. In Table 3, the concentration of the water-soluble alkali metal salt or water-soluble amine to be added is represented by "percentage" and "mM".

The pH of the resulting various eye drops is also shown in Table 3.

TABLE 3

| | Concentration (%) | Concentration (mM) | Solubility | pH |
|---|---|---|---|---|
| Sodium chloride | 0.54 | 92.4 | dissolved | 7.77 |
| Sodium citrate | 1.92 | 65.3 | dissolved | 7.87 |
| Sodium acetate | 1.39 | 102.1 | dissolved | 7.87 |
| Potassium chloride | 0.79 | 106.0 | dissolved | 7.86 |
| Potassium acetate | 1.00 | 102.0 | dissolved | 8.24 |
| Tris* | 1.21 | 99.9 | dissolved | 9.50 |
| Sodium carbonate | 0.92 | 32.2 | dissolved | 7.36 |

*Tris: Tris(hydroxymethyl)aminomethane

Since sodium carbonate was not dissolved in the eye drop by the above operation, the pH was lowered to about 7 (i.e. pH=7.36) by further adding hydrochloric acid, thereby making it possible to dissolve in the eye drop.

Preparation Example 4

According to the same manner as that described in Preparation Example 1 except for using sodium polyacrylate [trade name: Aqualic FH-K manufactured by Nippon Shokubai Co., Ltd., viscosity-average molecular weight: 2,000,000 to 3,000,000] as the straight-chain type sodium polyacrylate, a water-soluble eye drop of the present invention was obtained.

| Carteolol hydrochloride | 2% |
|---|---|
| Sodium polyacrylate | 0.5% |
| Sodium chloride | 0.5% |

| -continued | |
|---|---|
| Sterile distilled water | q.s. |
| Total | 100% |

Preparation Examples 5 to 13

To the formulation of Preparation Example 4, each of the following various additives was added in each amount to obtain each water-soluble eye drop (nine kinds) of the present invention.

| Sodium citrate: | 0.006 M, 0.06 M |
|---|---|
| Citric acid: | 0.0057 M |
| Polyvinyl alcohol: | 0.1%, 0.2%, 0.4%, 0.8%, 1.0% |
| Tris(hydroxymethyl) aminomethane | 0.01 M |

Test of Dissolution State

The respective water-soluble eye drops obtained in Preparation Examples 4 to 13 were observed during the storage at room temperature for 6 months. As a result, all preparations were transparent and any change in clarity and color of the solution could not be recognized.

Industrial Applicability

The water-soluble eye drop of the present invention has a remarkably long duration time of drug efficacy, and is superior in intraocular pressure inhibition action and is effective for treatment of glaucoma.

The disclosure of Japanese Patent Application Serial Nos.9-353039 and 10-298550, filed on Dec. 22, 1997 and Oct. 20, 1998, respectively, are incorporated herein by reference.

What is claimed is:

1. A water-soluble eye drop composition comprising (a) at least one selected from the group consisting of carteolol and an acid addition salt thereof, (b) at least one acrylic polymer selected from the group consisting of a straight-chain type polyacrylic acid and a pharmaceutically acceptable water-soluble salt thereof, and (c) at least one selected from the group consisting of a water-soluble alkali metal salt and a water-soluble amine.

2. The water-soluble eye drop according to claim 1, wherein the component (a) and the component (b) are contained in the amount of about 0.1 to 5% by weight and the amount of about 0.3 to 10% by weight, respectively, and the concentration of the component (c) is from about 10 to 140 mmol.

3. The water-soluble eye drop according to claim 2, wherein the pH of the water-soluble eye drop is from about 4 to 10 and the viscosity at 25° C. of the water-soluble eye drop is from about 5 to 100 centipoise and, furthermore, the viscosity-average molecular weight of the acrylic polymer of the component (b) is from about 100,000 to 3,000,000.

4. The water-soluble eye drop according to claim 3, wherein the pH of the water-soluble eye drop is from about 5 to 9 and the viscosity at 25° C. of the water-soluble eye drop is from about 10 to 70 centipoise and, furthermore, the viscosity-average molecular weight of the acrylic polymer of the component (b) is from about 2,000,000 to 3,000,000.

5. The water-soluble eye drop according to claim 2, wherein the component (a) and the component (b) are contained in the amount of about 0.5 to 3% by weight and the amount of about 0.3 to 0.5% by weight, respectively, and the concentration of the component (c) is from about 30 to 120 mmol.

6. The water-soluble eye drop according to claim 5, wherein the pH of the water-soluble eye drop is from about 4 to 10 and the viscosity at 25° C. of the-water-soluble eye drop is from about 5 to 100 centipoise and, furthermore, the viscosity-average molecular weight of the acrylic polymer of the component (b) is from about 100,000 to 3,000,000.

7. The water-soluble eye drop according to claim 5, wherein the pH of the water-soluble eye drop is from about 5 to 9 and the viscosity at 25° C. of the water-soluble eye drop is from about 10 to 70 centipoise and, furthermore, the viscosity-average molecular weight of the acrylic polymer of the component (b) is from about 2,000,000 to 3,000,000 and sodium chloride as the component (c) is contained in the amount of about 0.05 to 0.8% by weight.

8. The water-soluble eye drop according to claim 1, wherein the pH of the water-soluble eye drop is from about 4 to 10 and the viscosity at 25° C. of the water-soluble eye drop is from about 5 to 100 centipoise and, furthermore, the viscosity-average molecular weight of the acrylic polymer of the component (b) is from about 100,000 to 3,000,000.

9. The water-soluble eye drop according to claim 8, wherein the pH of the water-soluble eye drop is from about 5 to 9 and the viscosity at 25° C. of the water-soluble eye drop is from about 10 to 70 centipoise and, furthermore, the viscosity-average molecular weight of the acrylic polymer of the component (b) is from about 2,000,000 to 3,000,000.

10. The water-soluble eye drop according to claim 1, wherein the component (a) is carteolol hydrochloride.

11. The water-soluble eye drop according to claim 1, wherein the component (b) is sodium polyacrylate.

12. The water-soluble eye drop according to claim 1, wherein the component (c) is a water-soluble alkali metal salt.

13. The water-soluble eye drop according to claim 12, wherein the water-soluble alkali metal salt is sodium chloride or potassium chloride.

* * * * *